(12) United States Patent
Naghavi

(10) Patent No.: US 11,610,686 B1
(45) Date of Patent: Mar. 21, 2023

(54) SYSTEMS AND METHODS FOR RAPID RISK ASSESSMENT OF CHEST PAIN, REDUCING PATIENT WAIT TIME AND IMPROVING WORKFLOW IN THE EMERGENCY DEPARTMENT

(71) Applicant: The Bio Labs Lundquist Institute, Torrance, CA (US)

(72) Inventor: Morteza Naghavi, Torrance, CA (US)

( * ) Notice: Subject to any disclaimer, the term of this patent is extended or adjusted under 35 U.S.C. 154(b) by 0 days.

(21) Appl. No.: 17/657,754

(22) Filed: Apr. 2, 2022

(51) Int. Cl.
| | |
|---|---|
| *A61B 5/339* | (2021.01) |
| *G16H 50/30* | (2018.01) |
| *G16H 50/20* | (2018.01) |
| *G16H 40/20* | (2018.01) |
| *A61B 5/00* | (2006.01) |
| *G16H 15/00* | (2018.01) |

(52) U.S. Cl.
CPC .......... *G16H 50/30* (2018.01); *A61B 5/0044* (2013.01); *A61B 5/339* (2021.01); *A61B 5/7275* (2013.01); *G16H 15/00* (2018.01); *G16H 40/20* (2018.01); *G16H 50/20* (2018.01)

(58) Field of Classification Search
CPC ..... A61B 5/7275; A61B 5/0044; A61B 5/339; G16H 50/30; G16H 40/20; G16H 15/00; G16H 50/20
See application file for complete search history.

(56) References Cited

U.S. PATENT DOCUMENTS

2021/0209757 A1* 7/2021 Min ..................... G06V 10/764

* cited by examiner

*Primary Examiner* — George Manuel (57) ABSTRACT

A rapid chest pain risk assessment system includes an assessor, a computed tomography (CT) scanner, an electrocardiogram device for providing electrocardiogram related data, and an enzyme analyzer for analyzing the patient's blood. A computer enabled risk calculator categorizes the patients into low, intermediate, and high risk categories. The computer enabled risk calculator, using data from electrocardiogram, blood analyzer and patient's age, other risk factors and history, automatically generates orders for patients in low and intermediate risk categories to undergo a CT scan. A CAC analyzer using the computer file for analyzing the CT scan results then provides a CAC score based on those CT scan results. A risk score based on electrocardiogram, blood analyzer and patient's age, other risk factors and history of symptoms plus the CAC score is generated. Patients that are automatically assessed as being very low risk based on the risk score are recommended for discharge from the emergency room thereby lowering the unnecessary prolonged ER stay time.

20 Claims, 6 Drawing Sheets

| CAC Score | Coronary Artery Disease | 10-Year Mortality Risk |
|---|---|---|
| 0 | No evidence | Very low (<1%) |
| 1-10 | Minimal | Low (<10%) |
| 11-100 | Mild | Low (<10%) |
| 101-400 | Moderate | Moderate (10-20%) |
| >400 | Extensive | High (>20%) |

TABLE 1

PRIOR ART

FIG. 1

What is the HEART Score?

H = History

E = ECG

A = Age

R = Risk Factors

T = Troponin

| HEART score for chest pain patients | | |
|---|---|---|
| History | Highly suspicious | 2 |
| | Moderately suspicious | 1 |
| | Slightly suspicious | 0 |
| ECG | Significant ST-deviation | 2 |
| | Non specific repolarisation disturbance / LBTB / PM | 1 |
| | Normal | 0 |
| Age | ≥ 65 years | 2 |
| | > 45 and < 65 years | 1 |
| | ≤ 45 years | 0 |
| Risk factors | ≥ 3 risk factors or history of atherosclerotic disease* | 2 |
| | 1 or 2 risk factors | 1 |
| | No risk factors known | 0 |
| Troponin | ≥ 3x normal limit | 2 |
| | > 1 and < 3x normal limit | 1 |
| | ≤ 1x normal limit | 0 |
| | | Total |

*Risk factors for atherosclerotic disease:
Hypercholesterolemia   Cigarette smoking
Hypertension   Positive family history
Diabetes Mellitus   Obesity

PRIOR ART

SYSTEMS AND METHODS FOR RAPID RISK ASSESSMENT OF CHEST PAIN, REDUCING PATIENT WAIT TIME AND IMPROVING WORKFLOW IN THE EMERGENCY DEPARTMENT

CROSS-REFERENCES TO RELATED PATENT APPLICATIONS

Not Applicable.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISK APPENDIX

Not Applicable.

BACKGROUND

Technical Field

The inventive subject matter is generally directed towards systems and methods for improving patient care and workflow in healthcare settings, more specifically for reducing patient wait time and improving the diagnostic accuracy of patients arriving in the emergency department (ED) or the emergency room (ER) with a complaint of chest pain, consequently improving the workflow in the ED/ER, increasing efficiency and reducing potential legal liabilities due to missed high-risk atherosclerotic patients.

Description of the Related Art

Coronary Artery Calcium (CAC) measured by computed tomography (CT) scan of the heart proves the presence of atherosclerotic coronary artery disease with near 100% specificity and predicts the risk of fatal coronary events. A great number of studies have shown that CT based CAC score (typically Agatston Score) aids risk prediction and is more predictive than any other single biomarker, including blood pressure, cholesterol and other well known risk factors. Despite such strong predictive value of CAC, as of today it has not be utilized for this purpose.

According to the Centers for Disease Control (CDC), Americans make 130 million visits to the Emergency Department (ED) every year. About 8% to 10% of these visits are symptoms of acute chest pain—up to 13 million visits a year. Except for trauma injuries, chest pain is one of the most common reasons for going to the ED. Persons experiencing chest pain should in general call emergency medical services or get to the ED as quickly as possible for rapid evaluation and treatment. However, the majority of ED patients who present with suspected Acute Coronary Syndrome (ACS) fall below the 1% risk threshold of a 30-day Major Adverse Coronary Event (MACE). About 50% of patients with chest pain symptoms—across all age groups—will have a diagnosis of nonspecific chest pain, unrelated to any cardiac condition.

Figure 1:
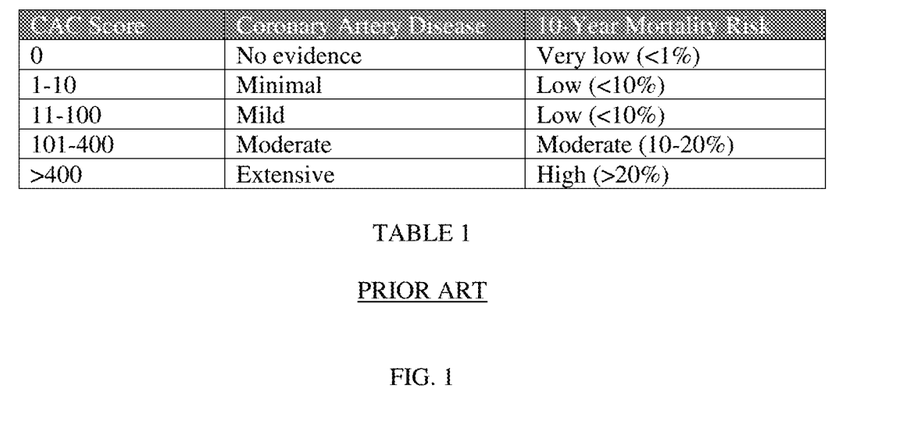
FIG. 1 is a table of a prior art scoring system.

ED providers are challenged to safely and responsibly identify as well as classify patients who present with symptoms of chest pain so they can avoid the risk of inadvertently discharging any patient at risk for a 30-day MACE. The HEART Scoring System for Chest Pain, recommended by the American Heart Association, has shown to be effective in predicting outcomes for patients with chest pain. The HEART Score assigns 0-2 points for each of five categories. FIG. 1 shows exemplary HEART Score information. As shown in the table in FIG. 1, the percentage of low and intermediate risk ED patients with chest pain are more than 50%.

Although the HEART Score includes an ECG and troponin result, which can indicate a very low risk of a 30-day MACE, most clinicians are not comfortable discharging a patient to home. CAC testing systems and methods can aid in the accurate evaluation of low and intermediate-risk patients. Specifically, integrating CAC testing very early in evaluating chest pain can appropriately triage and discharge patients who do not require additional testing or invasive procedures. The 2021 AHA/ACC/ASE/CHEST/SAEM/SCCT/SCMR Guideline for the Evaluation and Diagnosis of Chest Pain includes a recommendation for CAC: "For patients with stable chest pain and no known coronary artery disease (CAD) categorized as low risk, CAC testing is reasonable as a first-line test for excluding calcified plaque and identifying patients with a low likelihood of obstructive CAD. Further, artificial intelligence and machine learning have been used in data analysis to provide output without human intervention in various healthcare services, such as bioinformatics, genomics, and image analysis.

In view of the above, there is a long-felt need in the healthcare industry to improve the workflow in ER settings as well as to reduce patient wait times using various systems and methods.

SUMMARY

The illustrative embodiments provide systems and methods for the rapid risk assessment of chest pain. In one embodiment, A rapid chest pain risk assessment system includes an assessor for assessing a patient's history and symptoms of a patient's cardiac health. It further includes a CT scanner for scanning and recording the patient's cardiac health and providing the CT results to a computer file. It also includes an electrocardiogram device for providing electrocardiogram related data about the patient's cardiac health and an enzyme analyzer for analyzing the patient's blood and obtaining one or more troponin enzyme levels of the patient's blood. In this embodiment, the computer enabled risk calculator categorizes the patients into low, intermediate, and high risk categories. The computer enabled risk calculator, using data from electrocardiogram, blood analyzer and patient's age, other risk factors and history, automatically generates orders for patients in low and intermediate risk categories to undergo a CT scan. A CAC analyzer using the computer file for analyzing the CT scan results then provides a CAC score based on those CT scan results. The computer enabled risk calculator then generates and reports a risk score based on electrocardiogram, blood analyzer and patient's age, other risk factors and history of symptoms plus the CAC score. Patients that are automatically assessed as being very low risk based on the HEART risk score <6 and CAC score zero are recommended for rapid discharge from the emergency room thereby lowering the unnecessary prolonged ER stay time.

In another embodiment, artificial intelligence is used to calculate a CAC score.

In another embodiment, the artificial intelligence used to calculate a CAC score further includes detecting features from at least one or more portions of the received CT results, electrocardiogram related data and troponin enzyme level data that fall within each of the one or more temporal windows, identifying patterns in the detected features based on one or more of the following models: a classification model and a regression model, and using the identified patterns, calculate, a probability of whether the identified patterns correspond to a CAC score of a patient.

In another embodiment, the artificial intelligence identifies patterns of coronary calcifications beyond Agatston Score and uses different features including the amount and distribution of density (dense calcification), proximity to aortic root and left main coronary artery, and other features in the entire data collected from the patient recognized by the AI.

In another embodiment, the CAC score is output to a computer enabled display.

In another embodiment, the CAC score is communicated to cloud storage in a network and then subsequently sent to a medical professional.

In another embodiment, the computer enabled display is on a mobile computing device application.

In another embodiment, the computer enabled display is on a desktop application.

In another embodiment, a report generator is used for a post-discharge self-report triage.

In another embodiment, the one or more additional reports from the same chest CT scan are generated covering one or more subject matters from the following group: lung nodules, emphysema score, cardiac & aortic sizes, pericardial fat, fatty liver, and bone density.

BRIEF DESCRIPTION OF THE DRAWINGS

The accompanying drawings, which are incorporated in and constitute a part of the specification, illustrate various example operations, apparatus, methods, and other exemplary embodiments of various aspects discussed herein. It will be appreciated that the illustrated element boundaries (e.g., boxes, groups of boxes, or other shapes) in the figures represent one or more examples of boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION OF THE EMBODIMENTS

According to embodiments of the claimed subject matter, various systems and methods are provided for improving workflow in health care settings, and more specifically for improving the workflow in emergency rooms as well as for reducing patient wait time in health care settings. CT coronary calcium imaging gives direct evidence of coronary artery disease in patents. In several large, long-term studies CT calcium score has been shown to be an important factor used for predicting the risk of coronary heart disease, with a higher score giving increased 10-year risk.

As shown in FIG. 1, the prior art CAC Score table shows varying levels of corresponding Coronary Artery Disease and 10-Year Mortality Risk. Integrating CAC testing very early in evaluating chest pain can appropriately triage and discharge patients who do not require additional testing or invasive procedures. The 2021 HA/ACC/ASE/CHEST/SAEM/SCCT/SCMR Guideline for the Evaluation and Diagnosis of Chest Pain includes a recommendation for CAC for patients with stable chest pain and no known coronary artery disease (CAD) that are categorized as low risk. These guidelines further state that CAC testing is reasonable as a first-line test for excluding calcified plaque and identifying patients with a low likelihood of obstructive CAD.

Figure 2:
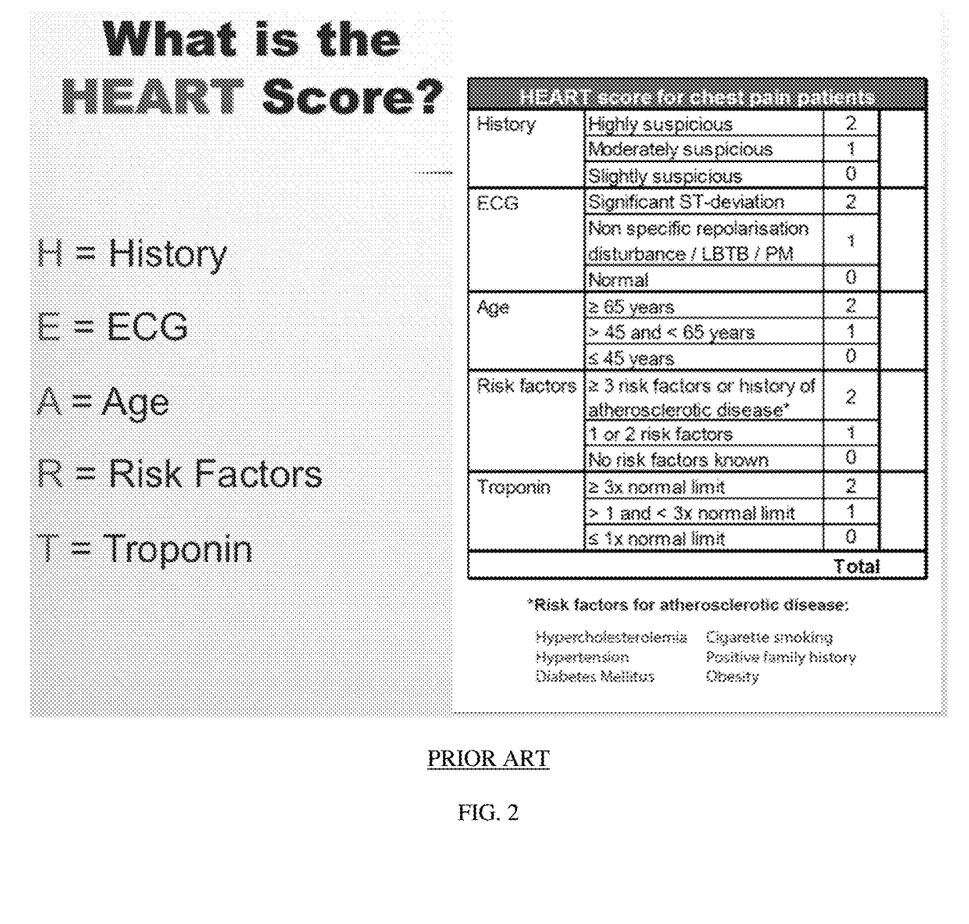
FIG. 2 is a flowchart of a method of chest pain risk assessment for symptomatic patients according to embodiments of the claimed subject matter.
Figure 3:
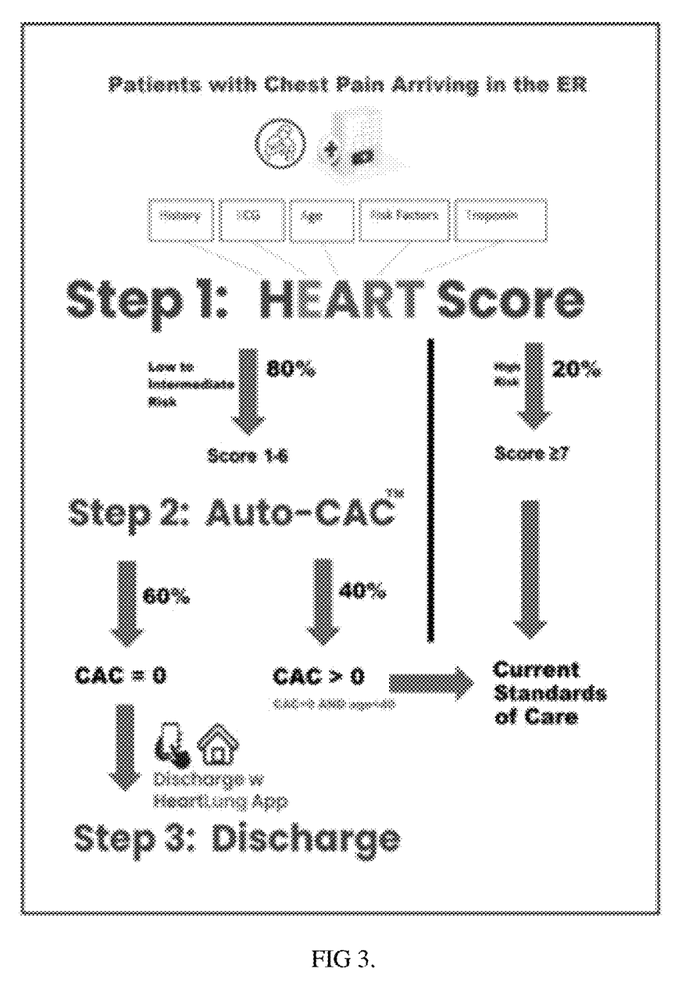
FIG. 3 illustrates a chart of the steps with exemplary values for calculating an Auto-CAC score according to embodiments of the claimed subject matter.

FIG. 2 illustrates a prior art HEART SCORE chart illustrating the risk factors involved in calculating heart disease risk and FIG. 3 illustrates a chart of the steps with exemplary values for calculating an Auto-CAC score according to embodiments of the claimed subject matter.

Many embodiments include the Auto-CAC™ scan, a non-contrast low-dose CT scan of the chest that provides a rapid coronary artery calcium (CAC) score using the onsite CT machine and cloud-based supervised AI powered by HeartLung™. The AI used can be any AI known to those skilled in the art and the steps can be performed on any suitable cloud including network based clouds such as those found on the internet. In many of these embodiments, the CT coronary calcium imaging is used to automatically calculate a CAC score. In some embodiments, the Auto-CACTM™ systems and methods using a HeartLung™ branded computing device application (app) can perform the CAC 24/7 and deliver a score to a health care professional and/or a patient within 30 minutes. The automatically generated score can assist these health care professionals such as ED physicians in determining if a patient can be safely discharged.

These described embodiments can help reduce the risk of misdiagnoses and inadvertent discharges of patients with Acute Coronary Syndrome (ACS). They can also help reduce the number of patients sent to additional (and unnecessary) testing or invasive procedures. The embodiments can also increase the rapid and accurate diagnosis of patients suitable for discharge home including those with an excellent prognosis. They can also help increase patient flow through the ED, allowing for more efficient use of time and resources.

In these embodiments, a combination of the use of a low-dose chest CT scan (e.g. with the described Auto-CAC™ or auto scoring embodiments] and hs-cTn enzyme level information in a patient can provide within a short period of time (30 minutes for example) can help health professionals rule out the presence of CAD, and any subsequent need for emergent CTA. In many embodiments, Myocardial infarction (MI) can be ruled out in patients with troponin concentrations <5 ng/L at presentation, or if delta <3 ng/L and remain below the 99th centile after 3 hours.

Figure 4:
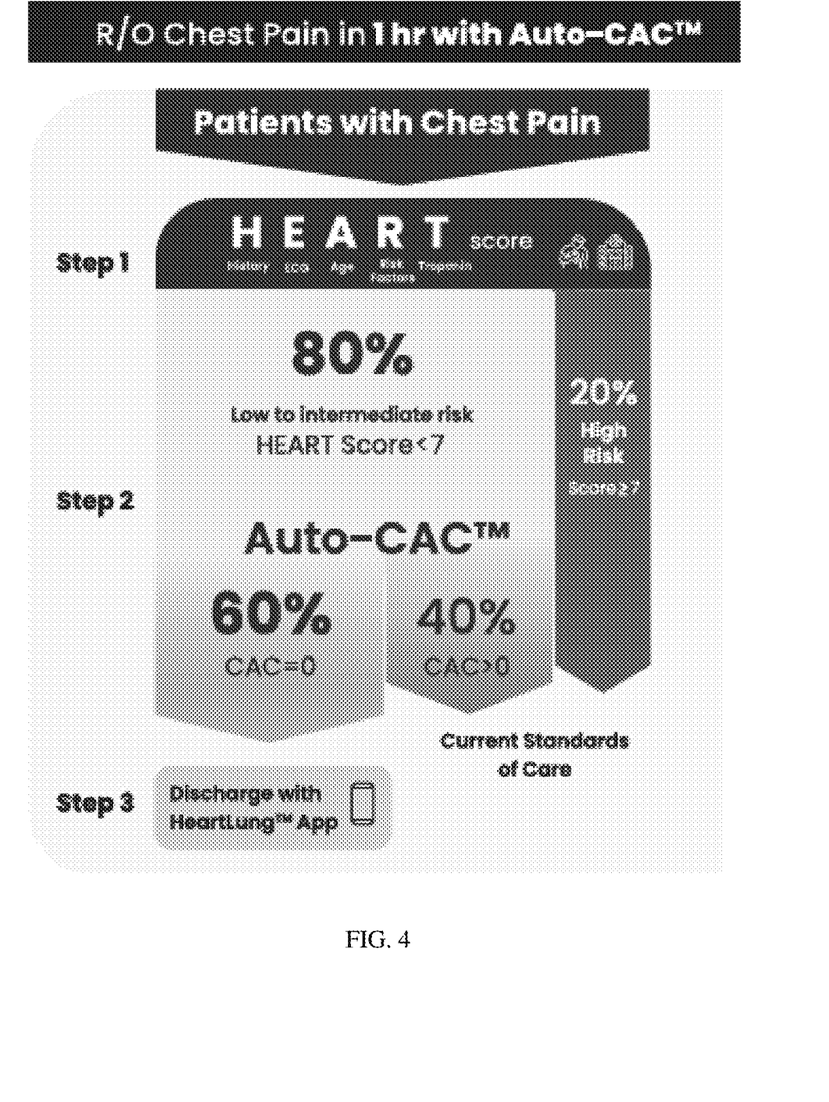
FIG. 4 is a flowchart of a method of chest pain risk assessment for symptomatic patients according to embodiments of the claimed subject matter.
Figure 5:
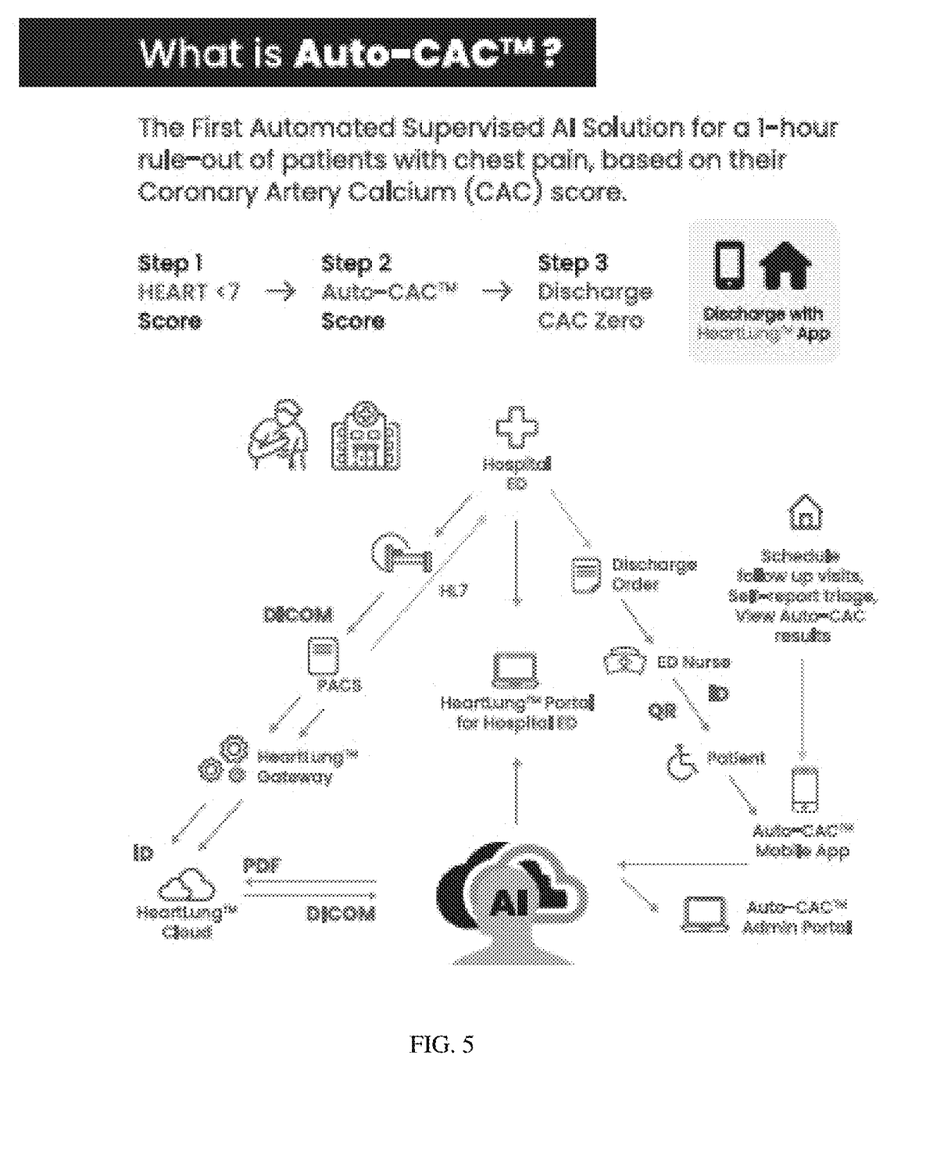
FIG. 5 is a flowchart of a method of chest pain risk assessment for symptomatic patients according to embodiments of the claimed subject matter.

Additionally, combining a CAC with the initial troponin from the HEART Score can lead to greater than 99% NPV with a number of benefits including the systems and methods being cost-effective, easy to perform (no patient preparation required and procedures completed in a single breath hold), no contrast required, widely available, easy to interpret results, and a higher NPV of CAC=0 compared to other methods known. These embodiments utilize CAC testing with subsequent interpretation of the results that can be completed rapidly and anytime including outside of regular clinic hours. Another benefit is that these embodiments can be used for prompt evaluation which can lead to a quicker discharge from ED or other health care setting when appropriate. A further benefit of these embodiments is that the radiation dosage used is minimal, for example a median dose for a low-dose CAC is 1.1 mSv. FIGS. 4 and 5 are flowcharts of systems and methods of chest pain risk assessment for symptomatic patients according to embodiments of the claimed subject matter.

The described embodiments are cost-effective and covers a larger population than hs-cTn diagnostics alone. At a low cost and minimal time requirement, in many cases a patient can be discharged home after a low-to-intermediate CAC score and a negative troponin level along with a documented report to share with a medical professional such as their primary care physician (PCP). This compares to much higher costs for a full troponin series coupled with many hours of waiting for testing and test results. This can help reduce the cost for health care by patients as well as reduce low-risk patient emergency department visit time which allows health care providers to allow for more time with complex, higher-revenue patient care.

Embodiments also include the use of an app or software for any computing platform which can provide a number of additional benefits such as a 30-day post-discharge self-report triage and reminders for scheduling visits with PCPs.

In accordance with the embodiments, additional tracking of patients with suitable records can be maintained including the use of the HeartLung™ application with discharged patients. Other tracking such as leadership in CAC with ACC/AHA guidelines-based care pathway can also be incorporated into the ED or other health care setting procedures. Additional business intelligence data from HeartLung™ app dashboard, such as analytics and usage of the app, can guide hospital management with ED-related key performance indicators (KPI). For example, both patients and their relatives can benefit from the incorporation of new guidelines based on this data by resulting in shorter ER stays. Embodiments can also include one or more full chest CT reports for EDs without the need for overnight 24/7 tele-radiology.

Figure 6:
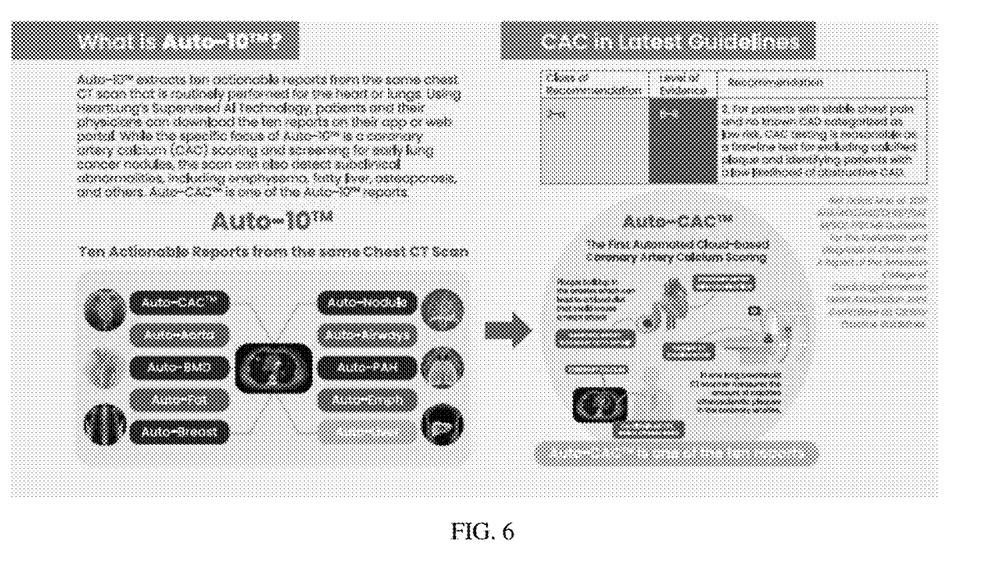
FIG. 6 is a flowchart of a method of chest pain risk assessment for symptomatic patients including various reports according to embodiments of the claimed subject matter.

FIG. 6 is a flowchart of a method of chest pain risk assessment for symptomatic patients including various reports according to embodiments of the claimed subject matter. Some embodiments include participation in the HeartLung™ (AI-Powered) Auto-10™ program which results in ten actionable patient-friendly reports from the same chest CT scan covering lung nodules, emphysema score, cardiac & aortic sizes, pericardial fat, fatty liver, bone density and other actionable information. These additional results can be provided to patients and their providers at low or cost and with no added radiation exposure to the patient.

References to "one embodiment", "an embodiment", "one example", and "an example" indicate that the embodiment (s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

While example systems, methods, and other embodiments have been illustrated by describing various embodiments, and while these embodiments have been described in considerable detail, it is not the intention of the applicants to restrict or in any way limit the scope of the appended claims to such detail. It is not possible to describe every conceivable combination of components or methodologies for the purposes of describing the systems, methods, and other embodiments described herein. Therefore, the inventive subject matter is not limited to the specific details, the representative apparatus, and illustrative examples shown and described. Thus, this application is intended to embrace alterations, modifications, and variations that fall within the scope of the appended claims.

Unless otherwise defined, all terms (including technical and scientific terms) used in this disclosure have the same meaning as commonly understood by one of ordinary skill in the art to which this disclosure belongs. It is to be understood that the phrases or terms used with the present inventive subject matter is for the purpose of description and not of limitation. As will be appreciated by one of skill in the art, the present disclosure may be embodied within devices, systems, and methods as well as methods or systems embodied in one or more computer program products. Further, the embodiments may take the form of a computer program product on a computer-readable storage medium having computer-usable program code embodied in the medium.

What is claimed is:

1. A rapid chest pain risk assessment system comprising:
an assessor for assessing a patient's history of cardiovascular risk factors and symptoms of chest pain;
an electrocardiogram device for obtaining electrocardiogram related data from the patient;
an enzyme analyzer for analyzing the patients blood and obtaining troponin enzyme levels of the patient's blood;
wherein a computer enabled risk calculator categorizes the patients into low, intermediate, and high risk categories;
wherein the enabled risk calculator automatically generates orders for patients in low and intermediate risk categories to undergo a non-contrast cardiac CT scan;
wherein a CAC analyzer using the computer file for analyzing the CT scan results and providing a CAC score based on those CT scan results;
wherein a computer enabled risk calculator generates a risk score based on electrocardiogram, blood analyzer and patient's age, other risk factors and history of symptoms plus the CAC score; and
wherein patients that are automatically assessed as being very low risk based on the risk score are recommended for discharge from the emergency room thereby lowering the unnecessary prolonged ER stay time.

2. The rapid chest pain risk assessment system for symptomatic patients of claim 1, wherein artificial intelligence is used to calculate a CAC score.

3. The rapid chest pain risk assessment system of claim 2, wherein artificial intelligence used to calculate a CAC score further includes:
   detecting features from at least one or more portions of the received CT results, electrocardiogram related data and troponin enzyme level data that fall within each of the one or more temporal windows;
   identifying pa erns in the detected features based on one or more of the following models: a classification model and a regression model; and
   using the identified patterns, calculate, a probability of whether the identified patterns correspond to a CAC score of a patient.

4. The rapid chest pain risk assessment system of claim 1, wherein the CAC score is output to a computer enabled display.

5. The rapid chest pain risk assessment system of claim 4, wherein the computer enabled display is on a mobile computing device application.

6. The rapid chest pain risk assessment system of claim 1, wherein the CAC score is communicated to cloud storage in a network and then subsequently sent to a medical professional.

7. The rapid chest pain risk assessment system of claim 1, further comprising a report generator for a post-discharge self-report triage.

8. The rapid chest pain risk assessment system of claim 1, wherein one or more additional reports from the CT scan results are generated covering one or more subject matters from the following group: lung nodules, emphysema score, cardiac & aortic sizes, pericardial fat, fatty liver, and bone density.

9. The rapid chest pain risk assessment system of claim 1, wherein the zero CAC score in patients younger than 40 years may not be utilized for discharge due to higher prevalence of non-calcified coronary plagues and wherein in these younger populations either repeated HEART Score or measurement of carotid wall thickness also called carotid intima-media thickness (CIMT) may be used for maximizing accuracy and reducing potential liability of missing coronary events.

10. A method of rapid chest pain risk assessment comprising the steps of:
   assessing a patient's health history and heart health symptoms;
   scanning the patient's using computed tomography (CT);
   storing the CT results to a computer file;
   scanning the patient's cardiac health using an electrocardiogram;
   storing the electrocardiogram generated data resulting from said scanning, the data comprising cardiac health data;
   analyzing the patient's blood and obtaining one or more troponin enzyme levels of the patient's blood;
   storing the troponin enzyme level data resulting from said testing;
   using a computer enabled risk calculator to categorize the patients into low, intermediate and high risk categories;
   using the data from electrocardiogram, blood analyzer and patient's age, other risk factors and history to automatically generate orders for patients in low and intermediate risk categories to undergo a CT scan;
   using a CAC analyzer to analyze the CT scan results in the computer file and provide a CAC score based on those CT scan results;
   using a computer enabled risk calculator and reporting system to generate a risk score based on electrocardiogram, blood analyzer and patient's age, other risk factors and history of symptoms plus the CAC score;
   assessing one or more patients automatically as to being very low risk based on the risk score; and
   recommending the discharge of any one or lore low risk patients from the emergency room thereby lowering the unnecessary prolonged ER stay time for those one or more patients.

11. The method of rapid chest pain risk assessment of claim 10, wherein artificial intelligence is used to calculate a CAC score.

12. The method of rapid chest pain risk assessment of claim 11, wherein the artificial intelligence used to calculate a CAC score further includes:
   detecting features from at least one or more portions of the received CT scan results, electrocardiogram related data and troponin enzyme level data that fall within each of one or more temporal window;
   identifying patterns in the detected features based on one or more of the following models: a classification model and a regression model; and
   using the identified patterns, calculate, a probability of whether the identified patterns correspond to a CAC score of a patient.

13. The method of rapid chest pain risk assessment of claim 10, wherein the CAC score is communicated to a processor with a computer enabled display.

14. The method of rapid chest pain risk assessment of claim 13, wherein the computer enabled display is a computer enabled display used with a mobile computing device application.

15. The method of rapid chest pain risk assessment of claim 13, wherein the computer enabled display is a computer enabled display used with a desktop application.

16. The method of rapid chest pain risk assessment of claim 10, wherein the CAC score is communicated to cloud storage in a network.

17. The method of rapid chest pain risk assessment of claim 10, wherein the CAC score is communicated to cloud storage in a network and then communicated to a medical professional.

18. The method of rapid chest pain risk assessment of claim 10, further comprising a step of reporting a post-discharge self-report triage.

19. The method of rapid chest pain risk assessment of claim 10, further comprising a step of generating additional reports from the CT scan results are generated covering one or more subject matters from the following group: lung nodules, emphysema score, cardiac & aortic sizes, pericardial fat, fatty liver, and bone density.

20. The method of rapid chest pain risk assessment of claim 10, further comprising a step of generating reminders to be communicated to the patient for follow up services.

* * * * *